United States Patent [19]

Kennard, III et al.

[11] Patent Number: 5,492,612

[45] Date of Patent: Feb. 20, 1996

[54] LEAN SHIFT CORRECTION OF POTENTIOMETRIC OXYGEN SENSORS

[75] Inventors: Frederick L. Kennard, III, Holly; Carlos A. Valdes, Flint, both of Mich.

[73] Assignee: General Motors Corporation, Detroit, Mich.

[21] Appl. No.: 310,231

[22] Filed: Sep. 21, 1994

Related U.S. Application Data

[63] Continuation-in-part of Ser. No. 197,687, Feb. 17, 1994, abandoned.

[51] Int. Cl.$^6$ .................................................. G01N 27/26
[52] U.S. Cl. ........................ 204/429; 204/426; 204/428; 204/424
[58] Field of Search .................................. 204/421, 424, 204/425, 426, 427, 428, 429

[56] References Cited

U.S. PATENT DOCUMENTS

| | | | |
|---|---|---|---|
| 3,935,089 | 1/1976 | Togawa et al. | 204/195 S |
| 4,199,425 | 4/1980 | Sinkevitch | 204/195 S |
| 4,240,890 | 12/1980 | Watanabe et al. | 204/195 S |
| 4,249,156 | 2/1981 | Micheli | 338/34 |
| 4,279,782 | 7/1981 | Chapman et al. | 252/465 |
| 4,307,061 | 12/1981 | Sarholz | 422/94 |
| 4,318,828 | 3/1982 | Chapman | 252/465 |
| 4,331,631 | 5/1982 | Chapman et al. | 422/180 |
| 4,382,323 | 5/1983 | Chapman et al. | 29/157 R |
| 4,394,301 | 7/1983 | Gardner | 252/455 Z |
| 4,507,397 | 3/1985 | Buss | 502/38 |
| 4,552,739 | 11/1985 | Kuhl | 423/328 |
| 4,704,494 | 11/1987 | Inui | 585/417 |
| 4,832,824 | 5/1989 | Vaughan et al. | 208/138 |
| 4,863,583 | 9/1989 | Kurachi et al. | 204/429 |
| 4,888,105 | 12/1989 | Huss, Jr. et al. | 208/137 |
| 4,950,828 | 8/1990 | Shum | 585/417 |
| 5,077,970 | 1/1992 | Hamburg | 60/274 |
| 5,083,427 | 1/1992 | Anderson | 60/274 |
| 5,160,598 | 11/1992 | Sawada et al. | 204/429 |
| 5,169,513 | 12/1992 | Mase et al. | 204/429 |

OTHER PUBLICATIONS

J. E. Anderson et al., "Mass transfer effects on $ZrO_2$ oxygen concentration cells exposed to non–equilibrium $H_2$–$O_2$ mixture"—Journal of Applied Electrochemistry 12 (1982) 463–467.

Keiichi Saji et al., "Voltage step characteristics of oxygen concentration cell sensors for nonequilibrium gas mixtures"—Toyota Central Research and Development Laboratories, Inc., Nagakute–cho, Aichi–gun, Aichi, 480–11 Japan, vol. 135, No. 7; pp. 1686–1691.

A. D. Colvin et al, "Catalytic effects on $ZrO_2$ oxygen sensors exposed to non–equilibrium gas mixtures"—J. Electroanal. Chem., 136 (1982) 179–183.

L. Eltinge, "Fuel-Air Ratio and Distribution from Exhaust Gas Composition", SAE Paper 680114, pp. 425–450.

G. Baier et al, "Non–Nernstian Zirconia Sensors for Combusion Control", Appl. Phys. A57, 51–56 (1993).

J. E. Anderson et al, "Steady–State Characteristics of Oxygen Concentration Cell Sensors Subjected to Nonequilibrium Gas Mixtures", J. Electrochem. Soc., vol. 128, No. 2, Feb. 1981, pp. 294–300.

*Primary Examiner*—Bruce F. Bell
*Attorney, Agent, or Firm*—Cary W. Brooks

[57] ABSTRACT

The invention includes the use of a pre-equilibration zone on an exhaust gas sensor to provide catalytic site to catalyze non-reacted components of the exhaust gas prior to the gas sample reaching the sensor's outer electrode. The pre-equilibration zone preferably includes a precious metal on the surface of a porous carrier. The invention also includes a method of making an exhaust sensor including a pre-equilibration zone, and a method of sampling an exhaust gas by passing the same through a pre-equilibration zone.

6 Claims, 7 Drawing Sheets

LEAN SHIFT CORRECTION OF POTENTIOMETRIC OXYGEN SENSORS

This is a continuation-in-part of prior U.S. application Ser. No. 08/197,687 filed on Feb. 17, 1994, now abandoned.

FIELD OF THE INVENTION

This invention relates to exhaust sensors, and more particularly to exhaust sensors including a catalytic pre-equilibration zone to minimize non-ideal sensor operating characteristics.

BACKGROUND

Conventional coatings used in protective layer over the sensing electrode surface of a ceramic anion-conductor exhaust gas sensor are ordinarily composed of various non-catalyzed porous ceramic oxides, such as spinel. The primary functions of these coatings are to act both as a mechanical shield to prevent gas and particulate-induced erosion of a platinum electrode of the sensor and as a filter to reduce the rate at which poisoning from silica, lead and other harmful constituents in the exhaust stream can occur. It has been observed in the past, however, that porous non-catalytic coatings have contributed to non-ideal sensor performance. In particular, the coatings are known to accentuate "lean shift", a phenomenon in which unreacted gases resulting from incomplete combustion, present in the exhaust gas, causes the sensor to switch at an air/fuel ratio which is greater than the true stoichiometric point where lambda equals exactly unity. This apparent lean shift of the sensor's switch point is caused by the faster diffusion of hydrogen as compared to oxygen through the porous protective coating covering the outer or exhaust gas electrode. In addition to "lean shift", unreacted gases can also contribute to sensor output amplitude variation and they can amplify temperature sensitivity. Although some types of coatings and sensor packaging arrangements in the marketplace seem to minimize non-ideal sensor operating characteristics better than others, these arrangements cause compromises in other aspects of the sensor's performance characteristics. No satisfactory solution to the problem has been discovered heretofore.

The present invention overcomes many of the shortcomings of the prior art.

SUMMARY OF THE INVENTION

The invention includes the use of a pre-equilibration zone on an exhaust gas sensor to provide catalytic sites to catalyze the non-reacted components of the exhaust gas prior to the gas sample reaching the sensor's sensing electrode. A catalyst layer on the surface of the porous protective layer covering the outer electrode defines the equilibration zone and preferably includes a precious metal on a porous carrier such as a ceramic oxide. The invention also includes a method of making an exhaust sensor including a pre-equilibration zone, and a method of sampling an exhaust gas by passing the gas through a pre-equilibration zone.

These and other objects, features and advantages of the invention will become apparent from the following brief description of the drawings, detailed description and appended claims and drawings.

DETAILED DESCRIPTION

Figure 1:
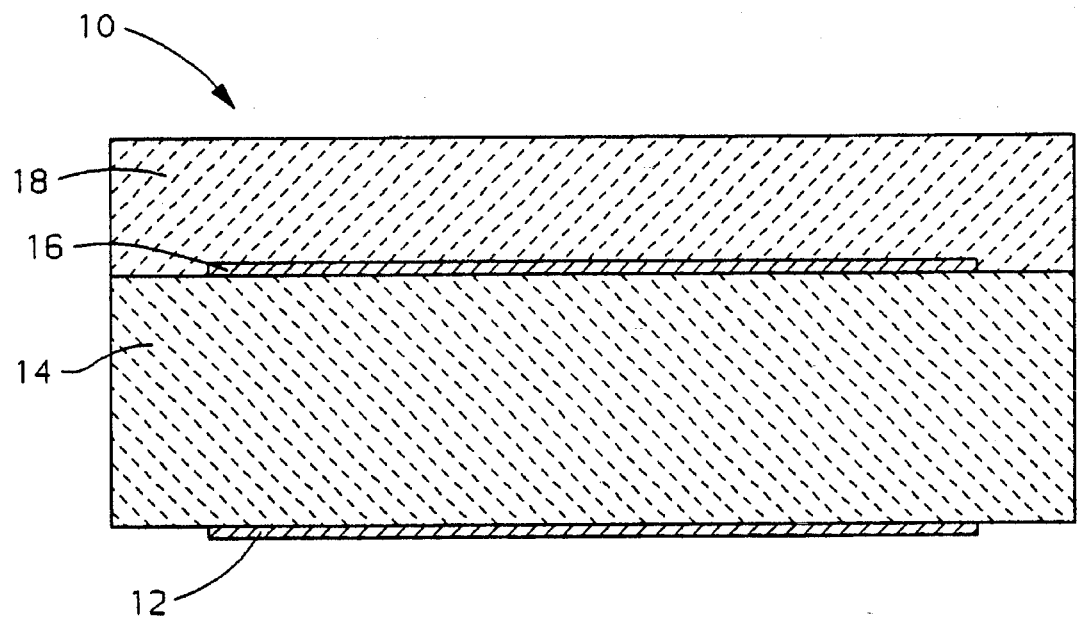
FIG. 1 is an illustration of a representative section of the sensing portion of an ordinary exhaust sensing device.

A pre-equilibration zone according to the present invention may be provided by a distinct layer of catalyst material on the surface of the porous protective coating covering the outer electrode. This catalyst layer must have porosity that is contiguous with the porosity of the protective coating so as to not restrict the access of the exhaust gas to the outer electrode. This pre-equilibrium zone may also have its own porous protective coating placed over it to protect it from abrasion and/or poisoning. This coating must be significantly thinner than the primary protective coating over the outer electrode so as to avoid any significant "lean shift" due to partitioning of hydrogen and oxygen during diffusion through it. The catalyst may take a variety of forms and preferably is an active metal such as palladium, platinum, rhodium, and other transition, metals such as nickel or mixtures of several such metals.

The catalytic pre-equilibration zone may be formed on the sensor by depositing a catalytic material on the exposed surface of the porous protective coating using a thin or thick film deposition technique. Examples of thin film deposition techniques would include sputtering, electron beam evaporation, chemical vapor deposition, and other similar techniques, while thick film deposition techniques would include screen printing, pad printing, ink jet printing, and others. Other techniques such as spraying or spinning on a metallo-organic solutions would also be suitable. The thickness of these thin and thick film catalytic coatings may range from a few hundreds of Angstroms or less to about 100 microns depending upon the application method and durability requirements. The durability of this catalyst layer improves with increasing thickness, however the thickness must be controlled, particularly with the thin film techniques so as not to bridge and therefore block the pores in the protective coating and prevent free access of the exhaust gas. Thick film inks tend to develop their own porosity as they are sintered. The sintering temperature should be kept low enough to prevent the formation of dense films. Porosity can be enhanced by the addition of particulate organic materials such as polymeric, microballoons, corn starch, etc., that burn out during sintering. Sintering of the thick films can be retarded by the addition of inorganic particulate material, that do not react with the platinum such as zirconia, alumina and other oxides. Cost is also a factor in determining the thickness required. Appropriate heat treatments such as sintering of the thick film or decomposition of the metallo-organic would also be required. In some circumstances where extra protection of the catalytic pre-equilibration layer from abrasion or poisoning is required, it may be necessary to protect this layer with an additional layer of porous protective coating. This layer could be thin so as to avoid any "lean shift" caused by this layer since the catalyst layer does not have any electrochemical function and, consequently, is less sensitive to poisoning. A suitable protective layer for this catalytic pre-equilibrium layer would be similar to those used to protect the outer electrode.

The outer electrode protective coating may have a thickness ranging from about 25 to about 500 microns and a porosity of about 10 to about 60%. A suitable protective coat material includes spinel or alumina, or any porous ceramic. The outer electrode of the sensor is made from a porous material that is both electrically conductive and catalytic to the exhaust gas, such as platinum. Other additives such as zirconia may be added to impart beneficial properties such as inhibiting sintering of the platinum to maintain porosity.

This electrode is applied to an electrolyte body such as zirconia in a manner which is known to those skilled in the art. The inner electrode is also made from a porous material as described above in a similar manner.

Figure 3:
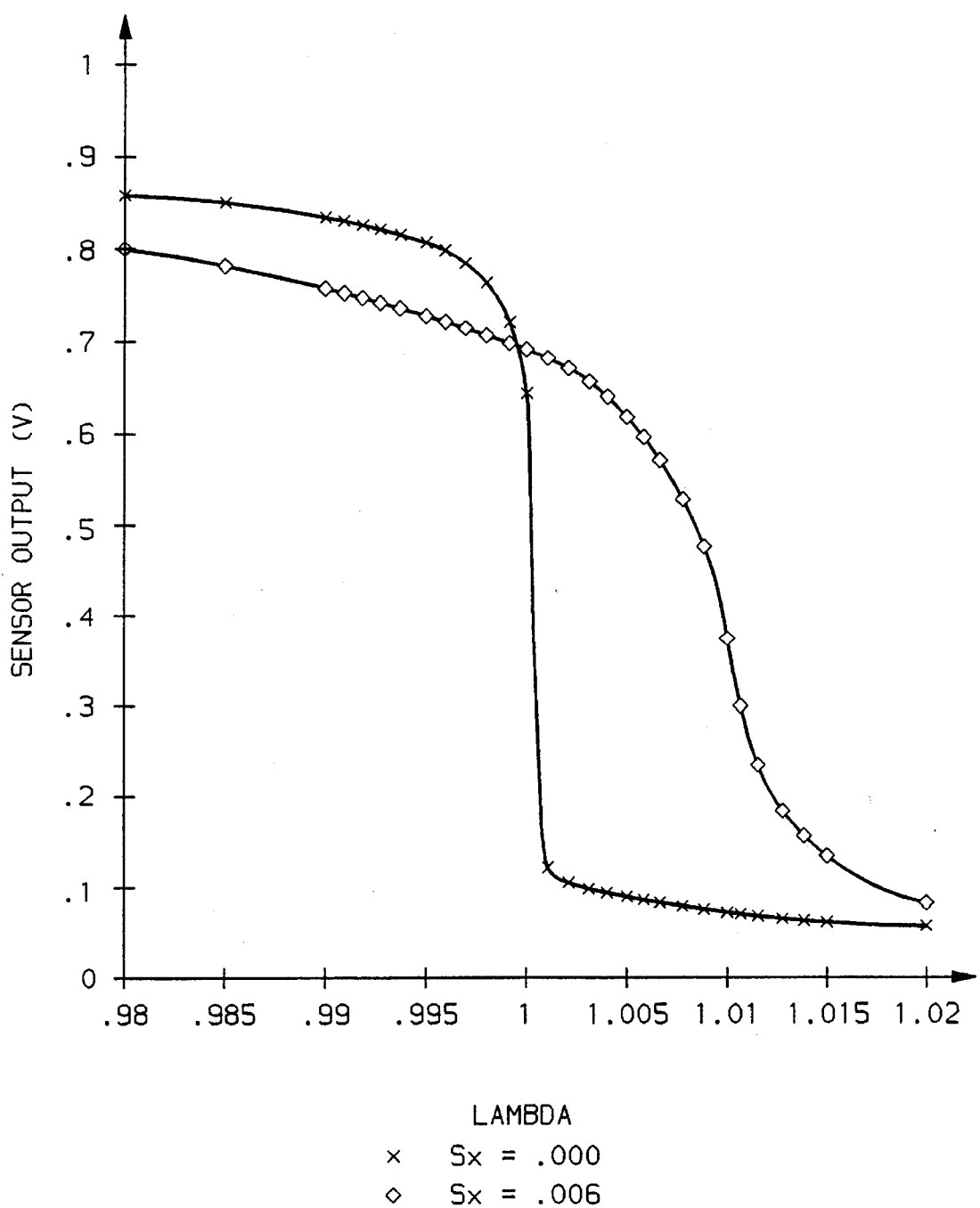
FIG. 3 is a graphic illustration of data obtained on the effect of unreacted exhaust constituents of a conical-shaped sensor without a pre-equilibration zone.
Figure 5:
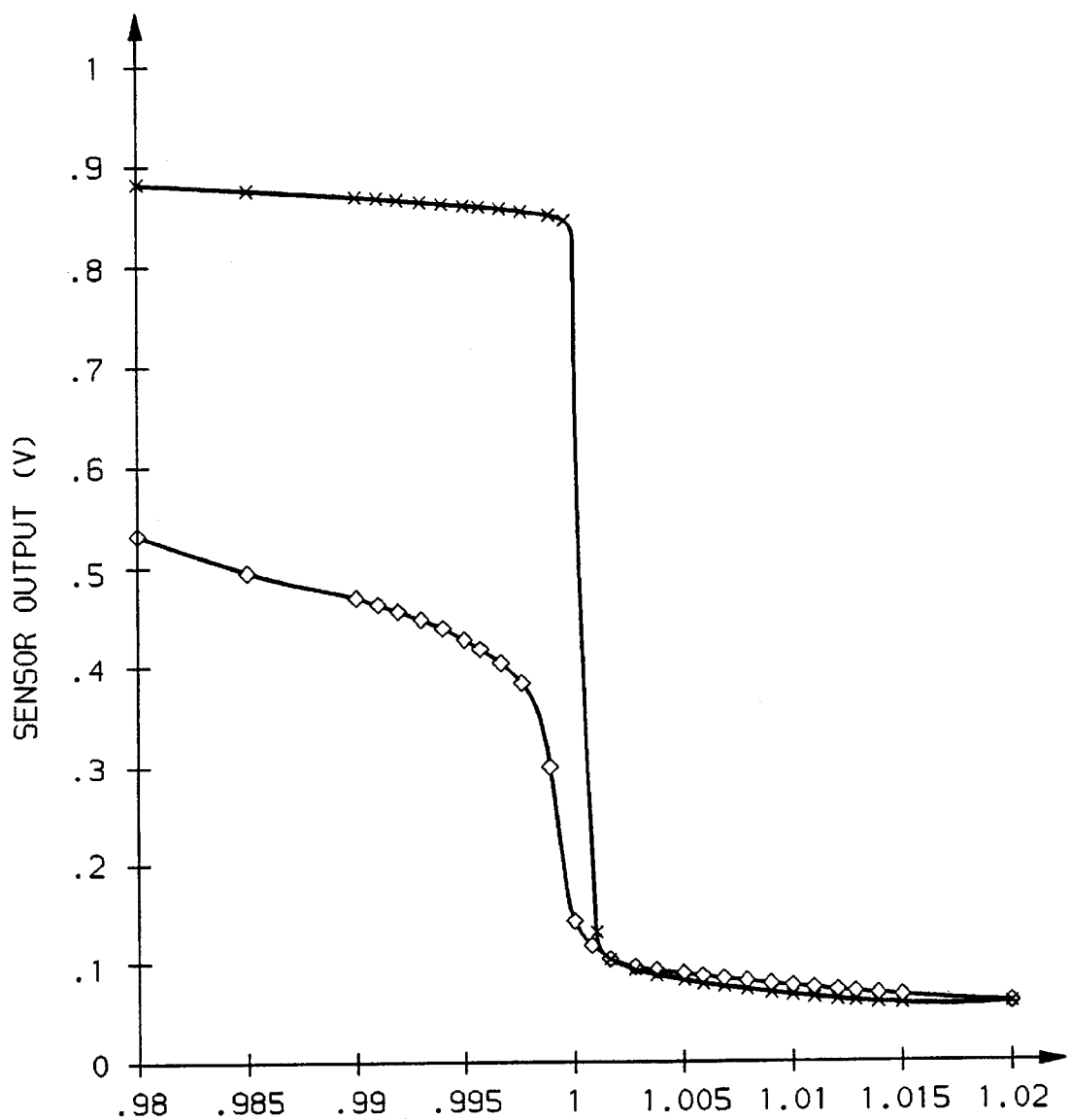
FIG. 5 is a graphic illustration of the CO sensitivity of a conical-shaped sensor without a pre-equilibration zone according to the present invention.
Figure 7:
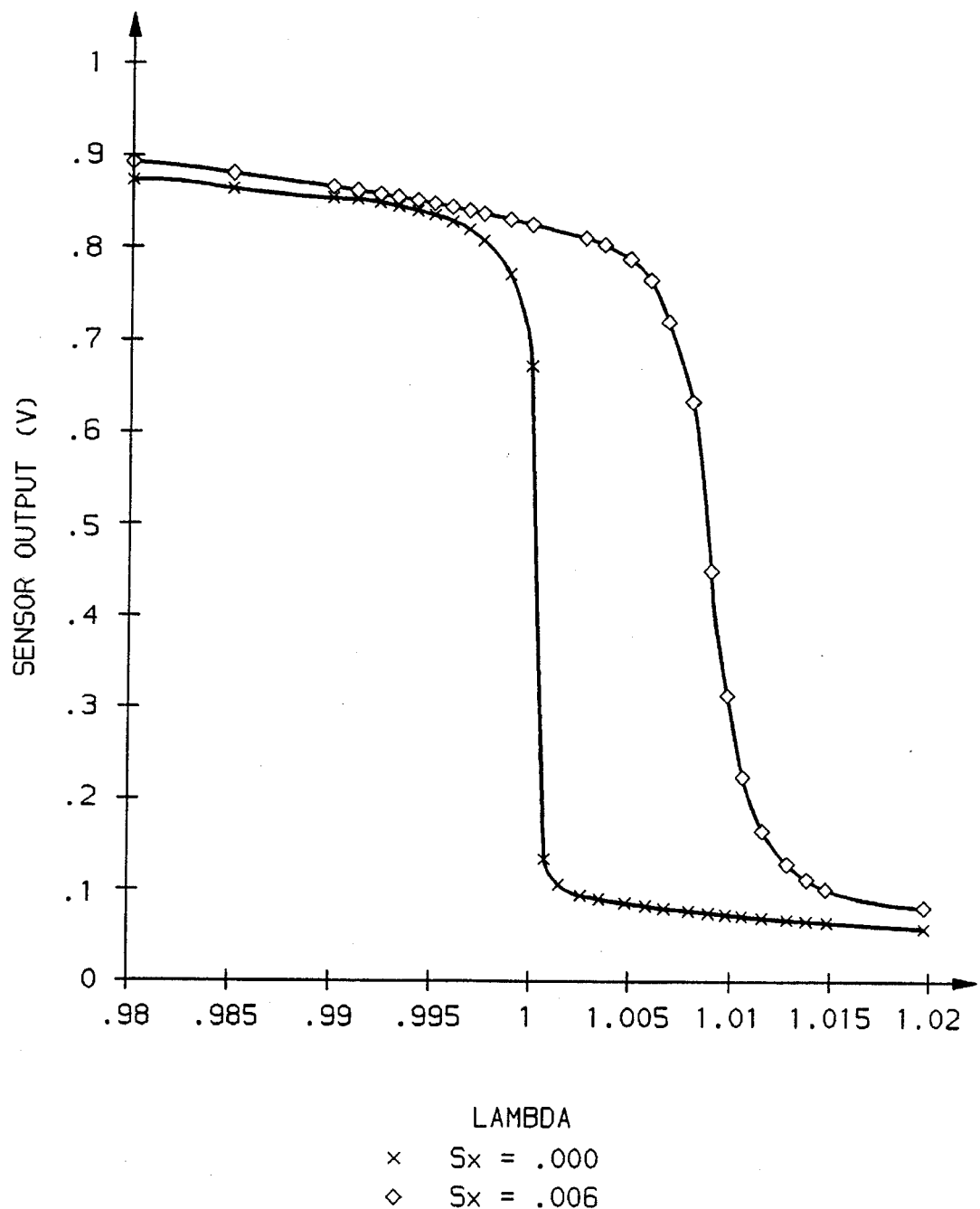
FIG. 7 is a graphic illustration of data obtained on the hydrogen sensitivity of a conical-shaped sensor without a pre-equilibration zone.

FIG. 1 illustrates a representative cross section of an ordinary exhaust sensing device 10 including an inner platinum electrode 12, a zirconia electrolyte 14, an outer platinum electrode 16 and a porous ceramic protective coat 18. The sensor in FIG. 1 does not include a catalyzed pre-equilibration zone according to the present invention. A sensor as illustrated in FIG. 1 was used in tests run wherein the results are illustrated in FIGS. 3, 5 and 7.

Figure 2:
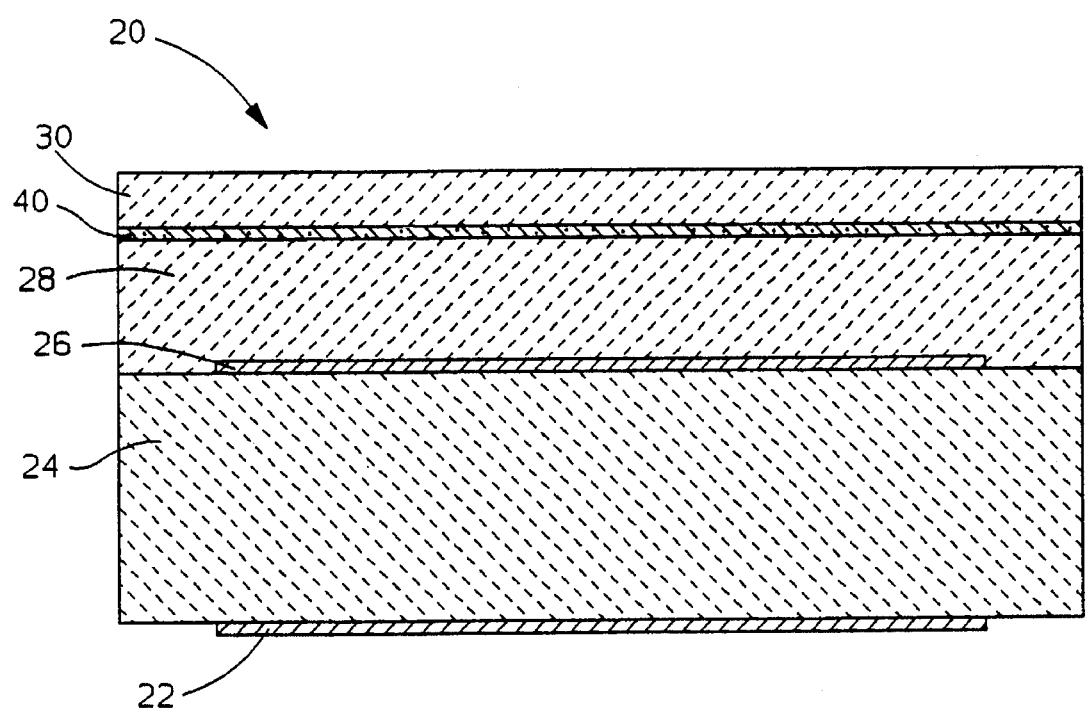
FIGS. 2 is an illustration of a representative section of the sensing portion of an exhaust sensor including a pre-equilibration zone according to the present invention.

FIG. 2 illustrates a sensing device 20 according to the present invention including an inner platinum electrode 22, a zirconia electrolyte 24, an outer platinum electrode 26, a porous ceramic protective coat 28, a catalytic layer 40 over the surface of the porous protective coat 28, and a thin porous protective coat 30 over the catalytic layer 40.

Figure 4:
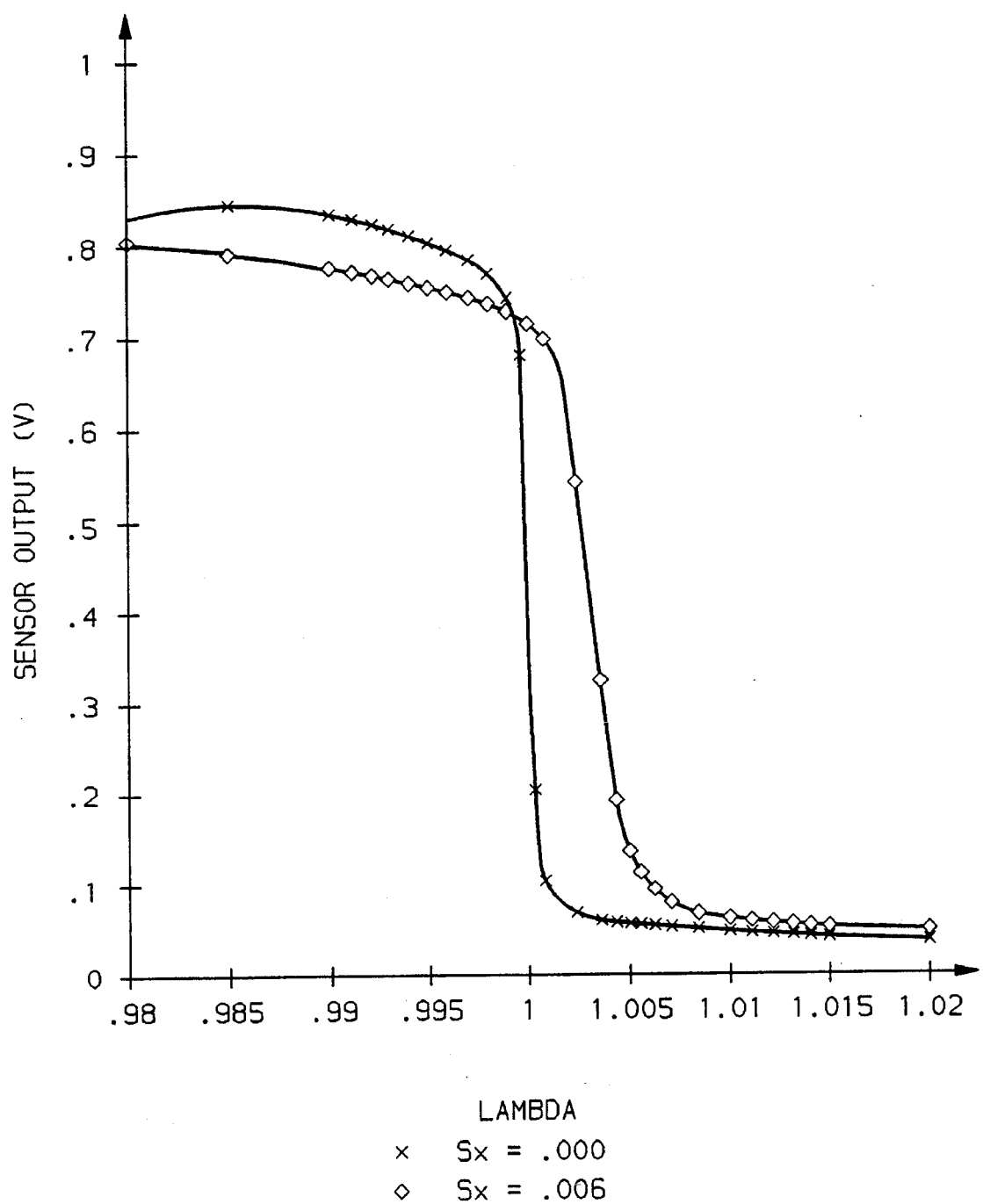
FIG. 4 is a graphic illustration of data obtained on the effect of unreacted exhaust constituents of a conical-shaped sensor with a pre-equilibration zone according to the present invention.
Figure 6:
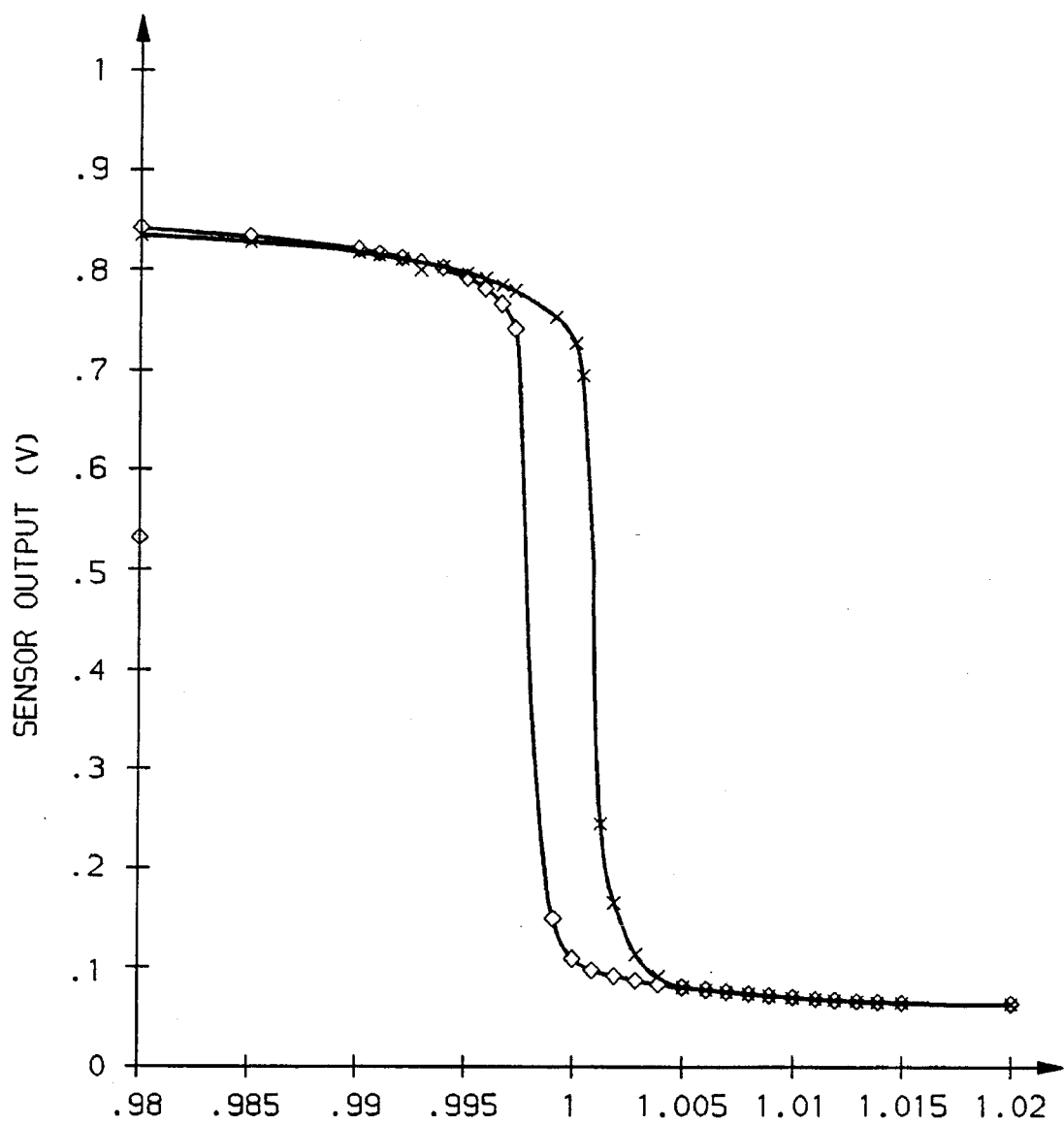
FIG. 6 is a graphic illustration of data obtained on the CO sensitivity of a conical-shaped sensor with a pre-equilibration zone according to the present invention.
Figure 8:
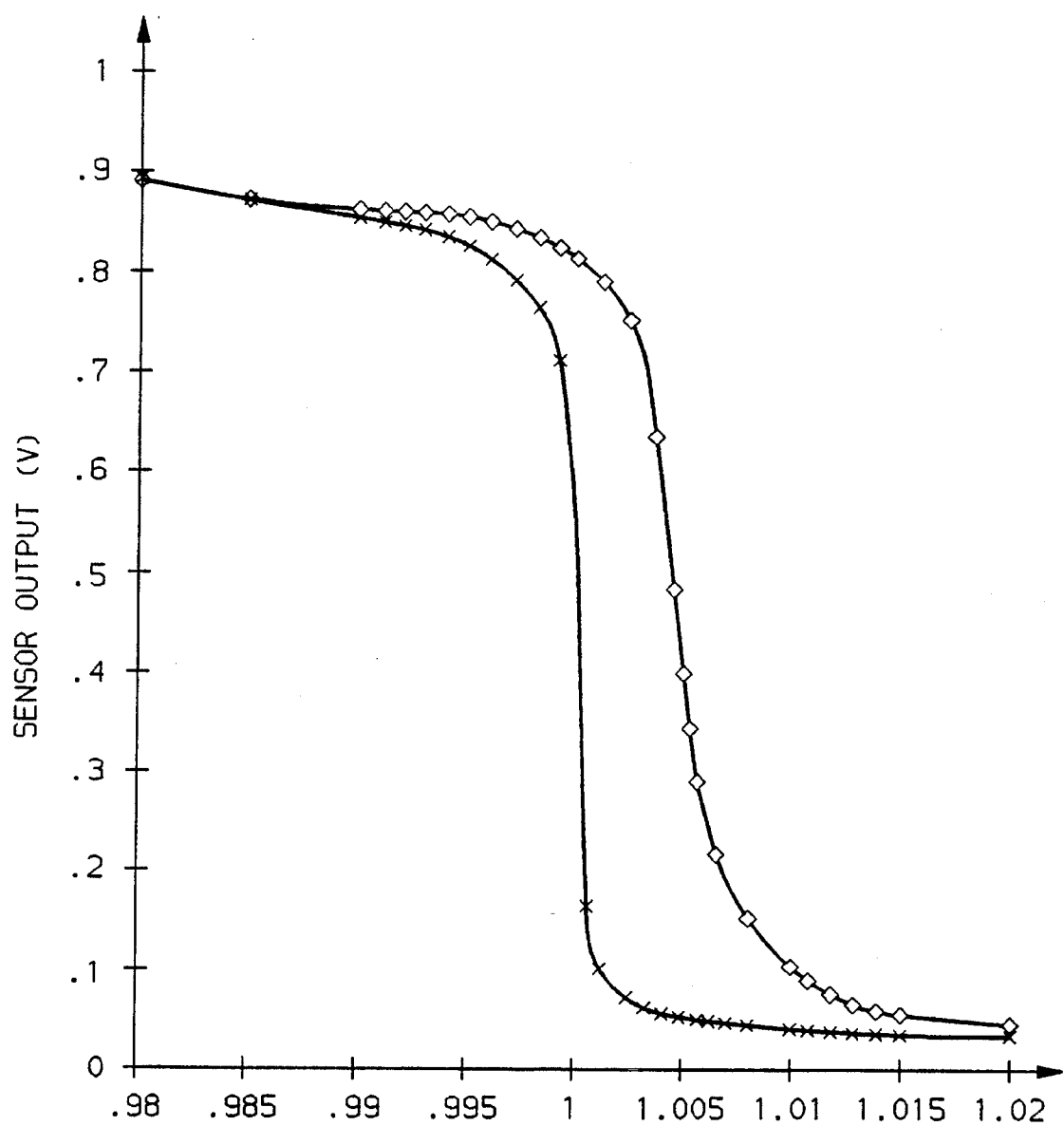
FIG. 8 is a graphic illustration of data on the hydrogen sensitivity of a conical-shaped sensor with a pre-equilibration zone according to the present invention.

The thin porous protective coat 30 may have a thickness ranging from about 10 to about 100 microns, and preferably about 30, 35, 40, 45, or 50–100 microns. The thin porous coat 30 has a thickness sufficient to protect the catalytic layer 40 from abrasion. However, the thin porous layer 30 is sufficiently thin to prevent a substantially greater amount of hydrogen relative to the diffusion rate of oxygen through the protective coating 30 so as to cause a non-correctable lean shift. The protective coat 28 overlying the outer electrode 26 has a thickness ranging from about 100 to about 500 microns and preferably 200–500 microns. The protective coat 28 has a thickness sufficient to prevent poisons such as lead, silica, phosphorus and other materials from diffusing through the porous protective coat 28 to the outer electrode 26. A sensor as illustrated in FIG. 2 was used in tests run wherein the results are illustrated by FIGS. 4, 6 and 8.

FIGS. 3–8 are graphical illustrations of results from gas bench testing of various sensors. Gas bench testing of sensors involves blending individual gases to form a mixture that simulates actual engine exhaust. The use of synthetic gas mixtures provides advantages over the conventional method of using actual engine exhaust for characterizing sensor performance. These advantages become more distinct when we attempt to focus in on small variations in sensor performance that are becoming more important as emission requirements and demands on control systems become tighter. Gas mixtures can be produced very precisely so that the test conditions can be very accurately controlled for highly accurate measurement of sensor performance. The test mixtures can be easily varied under controlled conditions so that the impact of these variations on sensor output can be studied. Engine exhaust, on the other hand, has an extremely variable composition that is very difficult to measure and even more difficult to control. Analysis of exhaust gas is, at best, a low resolution average of the actual composition. Because engine test conditions can not be well controlled or monitored, sensor data produced with engine exhaust does not have the resolution needed to detect these small but important performance variations.

In theory, the large voltage step produced by a stoichiometric air/fuel ratio sensor is due to the very large changes in equilibrated oxygen and combustible gas partial pressures that occur as they approach zero at the stoichiometric point. However, the combustion reactions in actual exhaust gases are not totally complete so no sharp changes in any gas concentrations are observed that correspond to the stoichiometric point. These concentrations steps are only present when the gases approach equilibrium conditions. A perfect sensor would indicate the true stoichiometric point regardless of the chemical condition of the exhaust. Actual sensors are not ideal and as a result, sensor output variations are seen when they are exposed to non-equilibrium gas mixtures. By measuring the degradation in the output of a sensor when it is exposed to known non-equilibrium mixtures, a relative rating of sensor performance can be established. This is the basic approach used in stoichiometric sensor bench testing illustrated in FIGS. 3–8.

The first step in creating a test procedure using non-equilibrium gas mixtures is to determine a method that defines the non-equilibrium conditions. It is important that the definition be complete and concise so that the test conditions can be well documented and easily communicated. It is also important to be able to easily reference and compare the test conditions to actual engine exhaust. The characteristic selected to define the gas mixtures is the Maldistribution Parameter ($S_x$). The Maldistribution Parameter is well described in Eltinge in SAE paper 680114, which is hereby incorporated by reference. All of the basic gas constituents concentrations can be completely defined at any desired air/fuel ratio by specifying the value of $S_x$, the hydrogen to carbon ratio in the original fuel, and the value of the water-gas equilibrium constant. The Maldistribution Parameter is often calculated during the emission tests so a basis for comparison to actual engine exhaust exists.

The basic gas constituents present in hydrocarbon and air combustion exhaust are: nitrogen, carbon dioxide, water, carbon monoxide, oxygen, and hydrogen. The concentrations of all six of these constituents can be defined with the parameters listed above. Unburned hydrocarbons and $NO_x$ are also present in exhaust and do have an impact on sensor performance.

The gas bench test procedure consisted of recording the sensor voltage while stepping through a series of air/fuel ratios around the stoichiometric point. The air/fuel ratios are designated by the normalized value, LAMBDA (LAMBDA is the actual Air/Fuel ratio divided by the Stoichiometric Air/Fuel ratio). Typically, the air/fuel ratio sweep is started at the fuel rich condition of 0.98 LAMBDA and is stepped in increments of 0.001 LAMBDA to the fuel lean condition of 1.02 LAMBDA. This range normally includes the sensor voltage transition but is also narrow enough to provide good resolution of the sensor's characteristics. Two simulated gasoline exhaust mixtures are often used and are designated as $S_x$=0.000 and $S_x$=0.006 (numerical values are in terms of Fuel/Air mass ratios). In both cases the hydrogen/carbon ratio of y=1.85 for standard fuel and the generally assumed standard value of K=3.5 are used in addition to the $S_x$ value to determine mixture concentrations. The $S_x$=0.000 designation defines a fully equilibrated gas mixture and the actual test gas mixture approaches this condition to within practical limits. (A true equilibrium gas mixture would have rich A/F oxygen partial pressures in the range of $10^{-20}$ atm. and lean CO and $H_2$ partial pressures in a similar range. Due to limits on gas purity, leakage, contamination, etc., these low levels can not be achieved in bulk gas mixtures.) The actual $S_x$=0.000 test gas mixture requires that some minimal level of equilibration reactions occur on the sensor surface. Experience has shown that the output curves for most "normally operating" sensors are very close to ideal when tested with the simulated $S_x$=0.000 mixtures. This test is used as an indication of the sensors "baseline" performance. The other test gas, designated $S_x$=0.006, defines a mixture that represents the highest level of non-equilibrium conditions expected to be seen in a modern engine operated near the stoichiometric point. This mixture contains significant levels of oxygen, carbon monoxide, and hydrogen simultaneously. Significant equilibration reactions must occur on the sensor surface with this test gas. An ideal sensor would produce the same output curve with both the $S_x$=0.000 and $S_x$=0.006 mixtures. The variation between the two curves provides a rating of sensor performance.

The sensor curve for the sensors are observed to shift in two areas when tested with $S_x$= 0.006 gas mixtures compared to $S_x$=0.000 mixtures. As the gas composition moves further away from equilibrium, the rich voltage decreases and the sensor transition point shifts in the lean direction. These two effects appear to be caused by different phenomenon. The predominate theory is that the high diffusion rate of hydrogen relative to the diffusion rate of oxygen through the sensor's protective coating causes the lean shift. The hydrogen is oxidized on platinum surface to form water. This continuous reaction creates hydrogen and oxygen fluxes across the protective coating. The higher hydrogen diffusion rate creates an apparent rich condition at the platinum surface which shifts the transition point in the lean direction. Test data supports this theory.

The reduced rich voltages appear to be linked to the sensors ability to oxidize the excess carbon monoxide. If carbon monoxide is removed from the gas mixture, the rich voltage does not drop. Some of the excess oxygen present in rich conditions may be adsorbing on the platinum surface and not readily combining with the CO to form $CO_2$.

In each of the tests run wherein the results are illustrated in FIGS. 3–8, a porous ceramic protective coating was flame sprayed over a platinum outer electrode and zirconia electrolyte as illustrated in FIG. 1. In the examples corresponding to FIGS. 4, 6 and 8, the sensor included a thin layer of platinum catalyst deposited on the outer surface of the porous protective layer by sputtering. In the example corresponding to FIGS. 3, 5 and 7, the sensor did not have a catalyzed pre-equilibrium zone according to the present invention. Comparing FIG. 4 with FIG. 3 illustrates a dramatic reduction in lean shift which was reduced 80% by using a sensor according to the present invention. In the examples corresponding to FIGS. 5 and 6, the effect of unreacted exhaust constituents in the form of CO only on sensor output was measured. The effect is known as "rich voltage suppression." Comparing FIG. 6 with FIG. 5 shows a 80% reduction in rich voltage suppression according to the present invention. In FIGS. 7 and 8, the effect of unreacted exhaust constituents in the form of $H_2$ only on sensor output was measured. The effect is known as "hydrogen induced lean shift." Comparing FIG. 8 with FIG. 7 shows a 704 reduction in hydrogen induced lean shift using a sensor according to the present invention.

The embodiments of the invention in which an exclusive property or privilege is claimed as defined as follows:

1. An exhaust sensor comprising:
    inner and outer electrodes, an electrolyte body between the electrodes, and a first porous protective coating on the outer electrode, said first porous protective coat having a thickness ranging from about 100 to about 500 microns;
    a catalytic pre-equilibration layer overlying the first porous protective coat so that the first porous protective coat separates the outer electrode from the catalytic pre-equilibration layer, said catalytic pre-equilibration layer consisting essentially of at least one metal selected from the group consisting of platinum, palladium, rhodium, transition metals and mixtures thereof, and said catalytic pre-equilibration layer having a thickness ranging from about 100 Angstroms to 100 microns.

2. An exhaust sensor as set forth in claim 1 wherein the catalyst material is present in a thickness ranging from about 0.1 micron to about 10 microns of the catalyst material.

3. An exhaust sensor as set forth in claim 1 further comprising a second porous protective coating positioned on top of the catalytic pre-equilibration layer, said second protective coating having a thickness ranging from 10 to 100 microns.

4. An exhaust sensor as set forth in claim 3 wherein the second porous protective coating is at least one selected from the group consisting of alumina, zirconia, spinel and mixtures thereof.

5. An exhaust sensor as set forth in claim 1 further comprising a second porous protective coating on top of the catalytic pre-equilibration layer, said second porous protective coating having a thickness ranging from 35 to 100 microns.

6. An exhaust sensor as set forth in claim 5 wherein the thickness of the second porous protective coating ranges from 50 to 100 microns.

\* \* \* \* \*